(12) United States Patent
Rupp et al.

(10) Patent No.: US 11,566,240 B2
(45) Date of Patent: Jan. 31, 2023

(54) DESORPTION OF NUCLEIC ACIDS

(71) Applicant: Robert Bosch GmbH, Stuttgart (DE)

(72) Inventors: Jochen Rupp, Stuttgart (DE); Christian Dorrer, Winnenden (DE); Juergen Steigert, Stuttgart (DE); Bernd Faltin, Gerlingen (DE); Karsten Seidl, Mülheim an der Ruhr (DE)

(73) Assignee: Robert Bosch GmbH, Stuttgart (DE)

( * ) Notice: Subject to any disclaimer, the term of this patent is extended or adjusted under 35 U.S.C. 154(b) by 531 days.

(21) Appl. No.: 16/603,717

(22) PCT Filed: Apr. 5, 2018

(86) PCT No.: PCT/EP2018/058727
§ 371 (c)(1),
(2) Date: Oct. 8, 2019

(87) PCT Pub. No.: WO2018/189025
PCT Pub. Date: Oct. 18, 2018

(65) Prior Publication Data
US 2020/0377876 A1 Dec. 3, 2020

(30) Foreign Application Priority Data

Apr. 11, 2017 (DE) ...................... 10 2017 206 155.3

(51) Int. Cl.
*C12N 15/10* (2006.01)
*B01L 3/00* (2006.01)
*C12Q 1/6806* (2018.01)

(52) U.S. Cl.
CPC .... *C12N 15/1006* (2013.01); *B01L 3/502761* (2013.01); *C12Q 1/6806* (2013.01); *C12Q 2523/308* (2013.01); *C12Q 2565/629* (2013.01)

(58) Field of Classification Search
CPC .............. C12N 15/1006; C12Q 1/6806; C12Q 2523/308; C12Q 2565/629;
(Continued)

(56) References Cited

U.S. PATENT DOCUMENTS 8,772,017 B2 * 7/2014 Battrell ................. B01L 3/5027
435/306.1
9,322,014 B1 4/2016 VanderNoot et al.
(Continued)

FOREIGN PATENT DOCUMENTS

| EP | 0 700 521 B1 | 6/2003 |
| EP | 2 927 144 A1 | 10/2015 |
| WO | 2008/002725 A2 | 1/2008 |

OTHER PUBLICATIONS

International Search Report corresponding to PCT Application No. PCT/EP2018/058727, dated Jun. 11, 2018 (German and English language document) (9 pages).
(Continued)

*Primary Examiner* — Narayan K Bhat
(74) *Attorney, Agent, or Firm* — Maginot, Moore & Beck LLP

(57) ABSTRACT

In a method for the desorption of nucleic acids from a sample, in order to simplify the desorption of nucleic acids from the sample, a solid phase is repeatedly rinsed with an elution buffer in a microfluidic system, in order to elute nucleic acids bonded to the solid phase from the solid phase in the microfluidic system.

11 Claims, 2 Drawing Sheets

(58) Field of Classification Search
CPC ........ C12Q 2527/125; C12Q 2531/113; B01L 3/502761; B01L 3/5027
See application file for complete search history.

(56) References Cited

U.S. PATENT DOCUMENTS

| | | | | |
|---|---|---|---|---|
| 2006/0246575 | A1* | 11/2006 | Lancaster | B01L 3/502776 435/288.5 |
| 2011/0275058 | A1* | 11/2011 | Zhou | C12Q 1/708 435/6.15 |
| 2012/0214168 | A1 | 8/2012 | Young et al. | |
| 2013/0164825 | A1* | 6/2013 | Hollander | C12N 15/1017 536/25.4 |
| 2014/0017672 | A1* | 1/2014 | Holmberg | G01N 1/405 435/6.12 |
| 2014/0039177 | A1* | 2/2014 | Nelson | C12N 15/1017 536/25.41 |

OTHER PUBLICATIONS

Johnson et al., A Programmable Microfluidic System for Selective RNA or DNA Extraction from Various RAW Biological Samples, 14th International Conference on Miniaturized Systems for Chemistry and Life Sciences, Oct. 3-7, 2010, Groningen, The Netherlands, pp. 387-389.

Breadmore et al., Microchip-Based Purification of DNA from Biological Samples, Analytical Chemistry, American Chemical Society, vol. 75, No. 8, Apr. 2003, pp. 1880-1886, XP-002460392.

Kastania et al., Plasma micro-nanotextured polymeric micromixer for DNA purification with high efficiency and dynamic range, Analytica Chimica Acta, vol. 942, Oct. 2016, pp. 58-67, XP055476608.

Mamaev et al., Method for Automated Extraction and Purification of Nucleic Acids and Its Implementation in Microfluidic System, Applied Biochemistry and Microbiology, vol. 47 No. 2, Mar. 2011, pp. 211-220, XP055476599.

* cited by examiner

DESORPTION OF NUCLEIC ACIDS

This application is a 35 U.S.C. § 371 National Stage Application of PCT/EP2018/058727, filed on Apr. 5, 2018, which claims the benefit of priority to Ser. No. DE 10 2017 206 155.3, filed on Apr. 11, 2017 in Germany, the disclosures of which are incorporated herein by reference in their entirety.

The disclosure relates to a method for the desorption of nucleic acids from a sample.

BACKGROUND

The German laid-open specification DT 23 39 111 A1 discloses a method for the purification of proteins and other biospecifically adsorbable substances by biospecific adsorption and by desorption, the adsorption being effected on ultrafiltration membranes. European patent specification EP 0 700 521 B1 discloses a probe that is removably insertable into a mass spectrometer, the probe having a sample presenting surface for presenting an analyte to an energy source that emits energy capable of desorbing/ionizing the analyte from the probe for analyte detection, wherein said surface is derivatized with an affinity reagent which is capable of binding the analyte and which is selected from metal ions, nucleic acids, peptides, carbohydrates, proteins and combinations thereof, wherein a desorption/ionization assisting matrix material is provided on said surface in association with the affinity reagent.

SUMMARY

The method for the desorption of nucleic acids from a sample is characterized in that a solid phase is rinsed multiple times with an elution buffer in a microfluidic system in order to elute nucleic acids bound to the solid phase from the solid phase in the microfluidic system.

The sample is preferably a lyzed sample, for example a liquid containing target cells, for example a cell suspension or a patient sample, such as blood, lavage, sputum or a rinsed-out swab or smear. The sample has, for example, a volume of between a few microliters and ten milliliters. The sample typically has a volume of between one-half and one milliliter. The solid phase is preferably a filter, for example a silica filter. The elution buffer is, for example, water or water with suitable additives. The solid phase can also be referred to as the stationary phase. Analogously, the elution buffer, which is also called the eluent, can also be referred to as the mobile phase. In order to obtain nucleic acids from cells, the latter are often firstly lyzed and the nucleic acids released are purified in a subsequent step. The nucleic acids are then processed further or analyzed. By way of example, the purified nucleic acids may be selectively amplified by means of a PCR. The upper case letters "PCR" in this case stand for Polymerase Chain Reaction. There are various methods for the lysis of cells: for example this can be effected chemically, enzymatically or mechanically. For the purification of the nucleic acids that have been released from the cells, the lyzate formed by the lysis is often admixed with a binding buffer and brought into contact with a solid matrix, for example a silica filter, with the nucleic acids being adsorbed on the filter. The nucleic acids can then be washed and eluted. This eluate contains nucleic acids and can be used in further enzymatic reactions, for example PCR, sequencing or restriction enzyme digestion. By way of the processing in the microfluidic system, an undesirably high concentration of inhibitory constituents in an eluate can be reduced. Microfluidic systems are known per se, for example from the German laid-open specification DE 10 2009 028 496 A1. By performing the disclosed method in the microfluidic system, individual fractions of an eluate can be prepared with particularly low losses. A "fraction" refers to a defined volume that, for example, by means of a micropump integrated into the microfluidic system is displaced into a channel system that is likewise integrated into the microfluidic system. The individual fractions differ in concentration of nucleic acids and any inhibitors present. By way of a suitable process regime, fractions having a high inhibitor concentration can optionally be discarded. A fraction whose inhibitor concentration is lower can then advantageously be used for a subsequent analysis of the eluate. As a result of the elution buffer flowing through the solid phase multiple times, a saturation equilibrium at which the maximum elution efficiency is achieved can be established.

One preferred exemplary embodiment of the method is characterized in that the elution is effected by a micropump integrated into the microfluidic system and having a defined displacement volume that corresponds to an elution volume. The elution is advantageously effected through a defined elution buffer volume that is displaced by the micropump and passed across the solid phase. The defined volume is referred to as the elution volume. The process and the volume of the microfluidic channel network or grid are advantageously coordinated precisely with each other. The volumes of individual fractions may also differ. For instance, in a first step a small pump can for example be used (5 to 15 microliters per stroke; typically 11 microliters) in order to displace the wash buffer still present in the region of the filter and the incoming/outgoing channels. However, for the transport of the eluate into following process chambers, for example for a PCR, a larger volume is needed, which can be realized using a pump having a larger pump chamber (10 to 25 microliters; typically 20 microliters). The volume per elution fraction is between 10 to 100 microliters, especially between 15 to 50 microliters, for example 20 microliters. In one advantageous embodiment, micro-diaphragm pumps whose pump chamber volume corresponds precisely to the volume of an elution fraction are used for pumping the liquids in the microfluidic system. This has the advantage that on each pump stroke exactly the volume of an elution fraction is pushed across the filter, and the volume can therefore be adjusted particularly precisely.

A further preferred exemplary embodiment of the method is characterized in that the elution volume is one to one hundred microliters. The elution volume can be just a few microliters. The elution volume is preferably fifteen to fifty microliters. The elution volume is particularly preferably around twenty microliters. The best results were achieved with this elution volume in the experiments and investigations performed within the context of the present disclosure.

A further preferred exemplary embodiment of the method is characterized in that an elution medium is pumped back and forth across the filter in the microfluidic system. This affords inter alia the advantage that the elution fraction is mixed particularly well and that nucleic acids are released from the filter particularly well, in particular completely.

A further preferred exemplary embodiment of the method is characterized in that a direction of incoming flow onto the solid phase in the microfluidic system is reversed. An elution volume can thus be passed across the same solid phase multiple times. Depending on the design of the microfluidic system, however, an elution volume may also be passed unidirectionally, that is to say only in one direction, across the solid phase multiple times. Both methods, that is to say either with a unidirectional or else with a bidirectional incoming flow onto the solid phase, afford the advantage inter alia that nucleic acids can accumulate in a fraction according to the concentration gradient.

A further preferred exemplary embodiment of the method is characterized in that an eluate fraction is passed across the solid phase multiple times in the microfluidic system. The result of the elution is also referred to as the eluate. In the disclosed elution method, substances in a wash buffer can potentially come into contact with the elution buffer, if these substances are still present in channel sections of the microfluidic system during the elution. This occurs, for example, when a portion of the microfluidic path or the solid phase subjected to incoming flow is shared in successive sequence partially by the wash buffer and the elution buffer, as is the case in the washing step and elution step. If the entire eluate is used for a subsequent analysis, for example an enzymatic reaction such as a polymerase chain reaction, the high concentration of the inhibitory substances can bring this to a standstill. Advantageously, the elution step can be effected multiple times in series in the microfluidic system. In this case, an elution volume can be passed across the filter or the solid phase multiple times. As an alternative or in addition, part-volumes of the elution volume can be passed across the solid phase or the filter one after another in series. This has the advantage that in each further eluate fraction the concentration of inhibitory substances is reduced, since this is already displaced by the preceding eluate fraction. However, the yield of nucleic acids typically decreases with each further elution step, for which reason the highest concentration of nucleic acids and inhibitory substances is expected in the first fraction. It may thus be advantageous to discard the first eluate fraction. The first fraction of the elution buffer can advantageously be used to displace the remainder of the wash buffer. This first fraction of the elution buffer can be pumped, for example, into a collecting chamber within the microfluidic network or channel network of the microfluidic system. The fraction volume is in this case ideally identical, for example a multiple of a dead volume. "Dead volume" refers to a free volume in the solid phase and in a channel of the fluidic system which is filled with wash buffer. A second fraction can subsequently be passed across the solid phase once or multiple times in order to increase the yield of the nucleic acid.

A further preferred exemplary embodiment of the method is characterized in that a first eluate fraction and a second eluate fraction are combined in a microfluidic chamber in the microfluidic system to form a mixture from which an aliquot is withdrawn for further analysis. "Aliquot" refers to a sub-portion of the mixture. As a result of the mixing step, the concentrations of the inhibitory substances and of the nucleic acid are reduced. The concentration of the inhibitory substances can be reduced by this method by way of example to the extent that a sensitive enzymatic detection reaction can then be performed successfully in the first place. This is advantageous in that, by way of a suitable enzymatic detection method, for example PCR, even the smallest amounts of nucleic acid can be amplified, as a result of which the initially disadvantageous reduction in nucleic acid concentration in the aliquot withdrawn proves to be advantageous.

A further preferred exemplary embodiment of the method is characterized in that an eluate fraction n and an eluate fraction n+1 are combined in the microfluidic system to form a mixture. For instance, a third and a fourth eluate fraction can be combined into a mixture, for example. The letter n stands for a natural number.

A further preferred exemplary embodiment of the method is characterized in that, prior to the elution, at least one, a plurality or each of the following preparatory steps is/are implemented in the microfluidic system: the sample is lyzed prior to the elution in the microfluidic system in order to lyze the target cells and release the nucleic acids; a binding buffer is added to the lyzate in the microfluidic system in a binding step—which is optional—and is mixed with the lyzate; the lyzate or the mixture formed in the binding step is passed across the solid phase in the microfluidic system. The nucleic acids are adsorbed onto the solid phase in the process. The binding buffers typically contain a high proportion of chaotropic substances, for example guanidine thiocyanate, guanidine hydrochloride or cesium chloride and/or alcohol, for example ethanol or isopropanol. These substances are known for inhibiting enzymatic downstream applications, such as PCR, or possibly completely bringing them to a standstill. In addition, the lyzed sample material brings with it substances that can disrupt subsequent enzymatic processing of the nucleic acid. For this reason, the solid phase with the adsorbed nucleic acid is purged with a wash buffer which removes the disruptive constituents from the solid phase or reduces the concentration thereof. These wash buffers typically contain chaotropic substances, typically in lower concentration than the binding buffer, and/or alcohols. By way of the disclosed fluidic process regime in the microfluidic system, the concentration of the inhibitory constituents in the eluate can be effectively reduced.

The disclosure furthermore relates to a computer program product having a computer program that comprises software means for performing a method described above when the computer program is executed on a computer. The computer preferably forms part of a microfluidic platform and advantageously serves for controlling the process regime in the microfluidic system.

The object given above is achieved, in addition or as an alternative, in a microfluidic system having a channel network in which a solid phase and at least one micropump are arranged, in that the micropump is arranged in the channel network and set up so as to rinse the solid phase multiple times with an elution buffer in the microfluidic system in order to desorb nucleic acids from a preferably lyzed sample, in particular according to a method described above. For example, the micropump is implemented as a micro-diaphragm pump as described in the German laid-open specification DE 10 2010 001 410 A1. A pump chamber volume of the micropump, in particular micro-diaphragm pump, corresponds to a volume of an eluate fraction. The microfluidic system advantageously comprises a polymer chip, constituting a lab-on-a-chip, as disclosed in the German laid-open specification DE 10 2011 085 371 A1.

A preferred exemplary embodiment of the microfluidic system is characterized in that the solid phase is a filter which is arranged in the channel network of the microfluidic system and is connected to the micropump via a connecting channel. The filter is a silica filter, for example. The micropump is advantageously arranged between a storage reservoir and the filter. At least two discharge paths are advantageously connected downstream of the filter. In accordance with one design, a side channel advantageously branches off between the micropump and the filter. The side channel can advantageously constitute a bypass with respect to the filter. In accordance with a further advantageous embodiment, the filter is arranged between two micropumps.

Further advantages, features and details of the disclosure are apparent from the following description in which various exemplary embodiments are described in detail with reference to the drawing.

DETAILED DESCRIPTION

Figure 1:
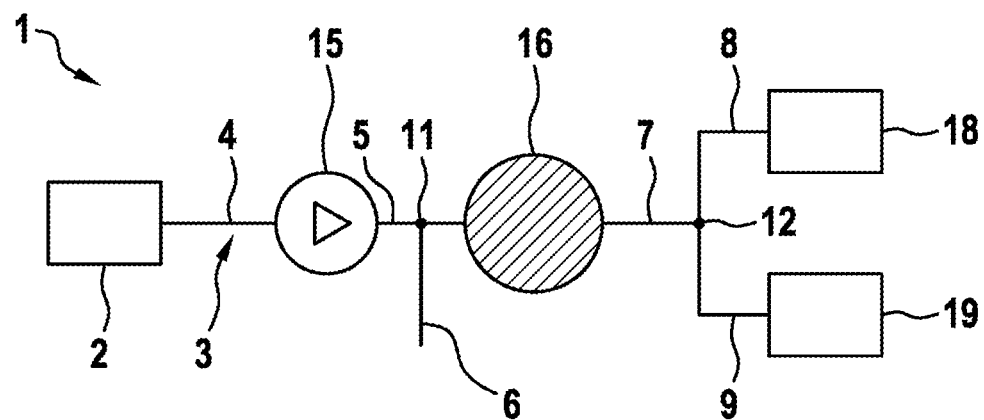
FIG. 1 shows a simplified illustration of a microfluidic system having a channel network in which a micropump and a solid phase are arranged, in accordance with a first exemplary embodiment.
Figure 2:
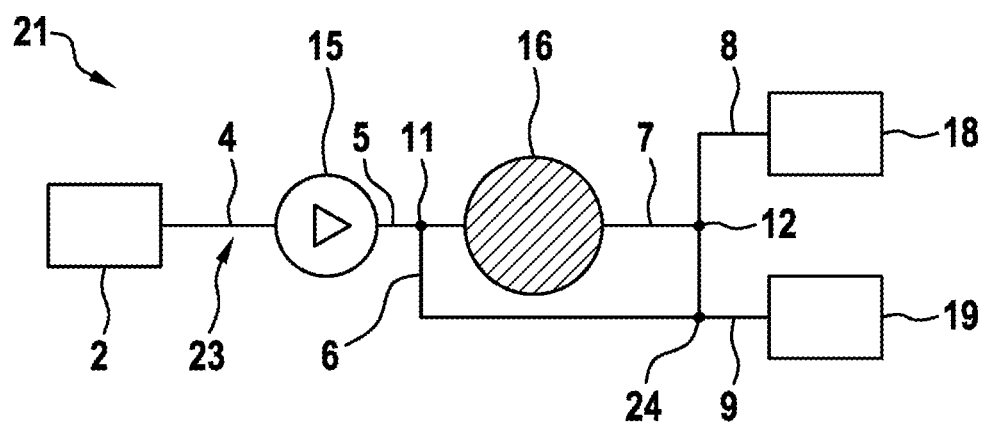
FIG. 2 shows a microfluidic system similar to that in FIG. 1 and in accordance with a second exemplary embodiment, having a side channel that bypasses the solid phase.
Figure 3:
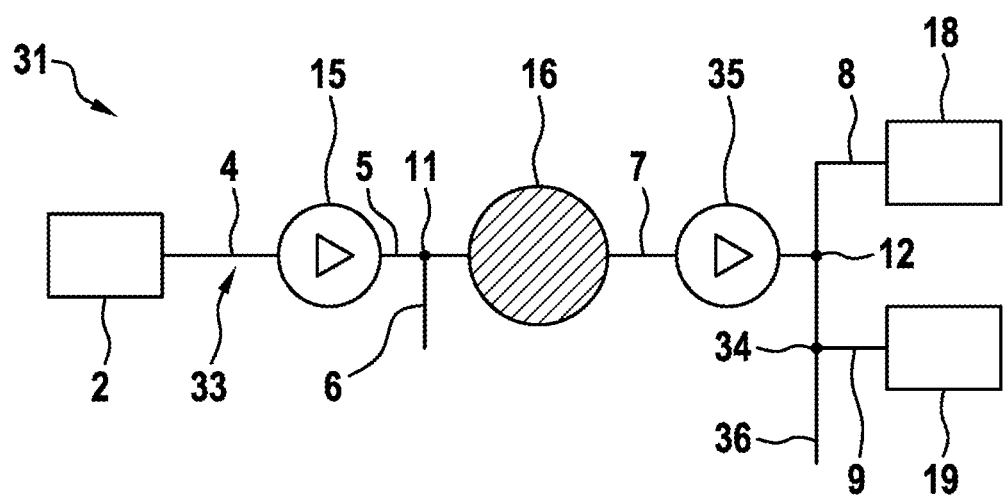
FIG. 3 shows a microfluidic system similar to those in FIGS. 1 and 2 and having a second micropump.

Three exemplary embodiments of a microfluidic system 1; 21; 31 for the desorption of nucleic acids from a solid phase are illustrated in a simplified manner in FIGS. 1 to 3. The microfluidic system 1; 21; 31 comprises a storage reservoir 2 which is connected via a microfluidic channel network 3; 23; 33 to a micropump 15 and a solid phase 16.

The nucleic acids are, for example, ribonucleic acids (RNA) or deoxyribonucleic acids (DNA). The solid phase is preferably a filter, for example a fabric or silica filter, having a diameter between one and twenty-five millimeters, especially between three and four millimeters.

The nucleic acids are desorbed from a lyzed sample. The sample is a liquid that contains target cells, for example a cell suspension and/or a patient sample.

The patient sample comprises blood, lavage, urine, cerebrospinal fluid, sputum or a rinsed-out swab or smear, for example. The volume of the sample is between a few microliters and ten milliliters, in particular between 0.2 and one milliliter.

The micropump 15 is, for example, a peristaltic pump, a diaphragm pump or an integrated microfluidic pump. A "fraction" refers to a defined volume that, for example by means of an integrated microfluidic pump, is displaced into the microfluidic channel system or channel network 3; 23; 33.

For preparation for the desorption, preferably at least one lysis step, one binding step and one washing step are performed. In the lysis step, a sample containing the target cells to be detected is lyzed by means of suitable methods. This involves lysing the target cells and releasing the nucleic acids. The resultant mixture is referred to as the lyzate.

In the optional binding step, a binding buffer is added to the lyzate and mixed with the lyzate. The mixture is subsequently passed across the solid phase 16, in particular the silica filter. The nucleic acids are adsorbed onto the solid phase or the filter 16 in the process.

In the washing step, at least one wash buffer is, or a plurality of wash buffers are, passed across the solid phase or the filter 16. In this step, the nucleic acids remain bound to the filter 16, whereas proteins or substances of the binding buffer are removed, for example.

In a subsequent elution step, the nucleic acids are eluted from the solid phase or the silica filter 16 with a suitable elution buffer. The elution is advantageously effected by the micropump 15 integrated into the microfluidic system 1. Here, the elution is effected using a defined volume, referred to below as a fraction, of the elution buffer, which is displaced through the micropump 15 and passed across the filter 16. In accordance with an advantageous variant, this step can be effected multiple times. In a further embodiment, the direction of incoming flow can be reversed and the eluate thus passed across the solid phase 16 multiple times.

In FIGS. 1 to 3, the microfluidic channel network 3; 23; 33 comprises microfluidic channels 4, 5, 6, 7, 8, 9. The microfluidic channels 4 to 9 are also referred to as channels for short.

Channel 4 connects the storage vessel 2 with the micropump 15. Channel 5 connects the micropump 15 to the solid phase or the filter 16. A connecting point or branching point 11, from which a channel 6—referred to as side channel 6—leads out, is arranged in channel 5.

A channel 7 connects the solid phase or the filter 16 to a connecting point or branching point 12, from which channels 8 and 9 lead out. A discharge path 18 is indicated by a rectangle 18 at the end of channel 8. A discharge path 19 is indicated by a rectangle 19 at the end of channel 9.

In the microfluidic system 1 illustrated in FIG. 1, after the washing of the filter 16, an elution medium, for example water, is sucked in from the storage reservoir 2 via the channel network 3 by means of the micropump 15, which will also be referred to as pump for short. A first fraction of the elution medium is pumped across the filter 16 into the first discharge path 18. Further channels and reservoirs, for example for storing further reagents or for receiving reagent waste, can also be present in the microfluidic system 1.

Next, a second fraction of the elution medium is pumped across the filter 16 into the second discharge path 19. In the second discharge path 19, this second eluted fraction is for example received by a chamber and processed further. A switchover between the first discharge path 18 and the second discharge path 19 is effected for example by means of microfluidic valves (not illustrated) at the connecting point or branching point 12, which is also referred to as a channel intersection. Further elution fractions may optionally also be pumped into further discharge paths.

In a variant of the channel network 3 that is illustrated in FIG. 1, the side channel branches off before the filter 16. This side channel 6 advantageously functions, in the phase during which the micropump 15 sucks in elution medium from the storage reservoir 2, as a discharge channel for the micropump 15. As a result of this, the micropump 15 is completely filled with elution medium before the actual elution operation. This affords the advantage that exactly the pump chamber volume is moved even in the elution of the first fraction.

In accordance with a processing variant, likewise indicated in FIG. 1, for the elution of a particular fraction the elution medium is pumped back and forth across the filter 16. To this end, the elution fraction is initially displaced across the filter 16 in the direction of a discharge path 18, 19 using the micropump 15. The elution fraction is then sucked in again across the filter 16. This sequence is optionally repeated multiple times, for example three times or five times. This affords the advantage that the elution fraction is mixed particularly well and nucleic acids are released particularly completely from the filter 16.

In accordance with a further processing variant, the fractions present in the two discharge paths 18, 19 are mixed after the elution, for example by means of pumping back and forth between chambers situated in the respective discharge paths 18, 19 by means of a further pump (not illustrated in FIG. 1). Pump chambers for receiving the eluate fractions may also be located directly in the discharge paths 18, 19 and can be used for the further transport of the eluate fractions. This processing variant has the advantage that the two fractions are mixed effectively and hence the concentration of inhibitors is lowered.

In the microfluidic system 21 illustrated in FIG. 2, in comparison to the channel network 3 from FIG. 1, a channel network 23 comprises an additional connecting point or branching point 24, which is also referred to as a channel intersection. The side channel 6 extends between the connecting or branching points 11 and 24 in the channel network 23. The side channel 6 can thus advantageously be used to bypass the filter 16. The side channel 6 opens out behind the filter 16 into the channel 9 with the discharge path 19. This variant has the advantage that the elution medium can be circulated across the filter 16. Through this, particularly good mixing of the fractions can be achieved.

The microfluidic system 31 illustrated in FIG. 3 comprises a channel network 33 having an additional connecting point or branching point 34. The additional connecting point or branching point 34 is arranged in the channel 9 to the discharge path 19. A further discharge path 36 leads out from the additional connecting point or branching point 34. In addition, in FIG. 3 a second micropump or pump chamber 35 is arranged in the channel 7 between the filter 16 and the connecting point or branching point 34. Using the second micropump or pump chamber 35, pumping back and forth can be actively assisted in both directions.

The invention claimed is:

1. A method for the desorption of nucleic acids from a sample, comprising: rinsing a solid phase with a first fraction volume of elution buffer in a microfluidic system; moving the first fraction volume to a collection chamber after rinsing the solid phase the first time; rinsing the solid phase multiple times with a second fraction volume of elution buffer the microfluidic system, after rinsing the solid phase with the first fraction volume, such that nucleic acids bound to the solid phase are eluted from the solid phase in the microfluidic system, wherein the elution is effected by a micropump integrated into the microfluidic system and having a defined displacement volume that corresponds to an elution volume.

2. The method as claimed in claim 1, wherein the elution volume is between 1 and 100 microliters.

3. The method as claimed in claim 1, wherein the solid phase is a silica filter, the method further comprising:
pumping the second fraction volume of the elution buffer back and forth across the silica filter in the microfluidic system.

4. The method as claimed in claim 1, further comprising:
reversing a direction of incoming flow onto the solid phase in the microfluidic system.

5. The method as claimed in claim 1, further comprising:
passing an eluate fraction of the second fraction volume of the elution buffer across the solid phase multiple times in the microfluidic system.

6. The method as claimed in claim 1, further comprising:
combining an eluate fraction of the second fraction volume of the elution buffer and a further eluate fraction of the second fraction volume of the elution buffer in the microfluidic system to form a mixture; and
withdrawing an aliquot from the mixture for further analysis.

7. The method as claimed in claim 1, further comprising, prior to the elution, at least one of the following:
lyzing the sample prior to the elution in the microfluidic system so as to lyze target cells and release the nucleic acids;
adding a binding buffer to the lyzate in the microfluidic system in a binding step and mixing the binding buffer with the lyzate; and
passing the lyzate or the mixture formed in the mixing of the binding step buffer with the lyzate across the solid phase in the microfluidic system.

8. The method as claimed in claim 1, further comprising:
rinsing the solid phase a first time with a portion of a third fraction volume of the elution buffer after rinsing the solid phase a first of the multiple times with the second fraction volume of elution buffer; and
rinsing the solid phase a second time with the portion of the third fraction volume of the elution buffer after rinsing the solid phase the first time with the portion of the third fraction volume of the elution buffer, wherein the solid phase is rinsed a second of the multiple times with the second fraction volume of elution buffer after rinsing the solid phase the second time with the portion of the third fraction volume of the elution buffer.

9. The method as claimed in claim 1, further comprising, prior to the elution, lyzing the sample in the microfluidic system so as to lyze target cells and release the nucleic acids.

10. The method as claimed in claim 1, further comprising, prior to the elution, adding a binding buffer to a lyzate in the microfluidic system in a binding step and mixing the binding buffer with the lyzate.

11. The method as claimed in claim 1, further comprising, prior to the elution, passing a lyzate or a mixture of a buffer with the lyzate across the solid phase in the microfluidic system.

* * * * *